US006933282B2

(12) United States Patent
Gluckman et al.

(10) Patent No.: US 6,933,282 B2
(45) Date of Patent: Aug. 23, 2005

(54) REGULATION OF TYROSINE HYDROXYLASE BY GPE

(75) Inventors: Peter D. Gluckman, Auckland (NZ); Jian Guan, Auckland (NZ); Tajrena Alexi, Auckland (NZ)

(73) Assignee: Neuren Pharmaceuticals Ltd., Auckland (NZ)

( * ) Notice: Subject to any disclaimer, the term of this patent is extended or adjusted under 35 U.S.C. 154(b) by 0 days.

(21) Appl. No.: 10/606,574

(22) Filed: Jun. 26, 2003

(65) Prior Publication Data

US 2004/0087487 A1 May 6, 2004

Related U.S. Application Data

(63) Continuation of application No. 09/719,459, filed as application No. PCT/NZ99/00085 on Jun. 15, 1999, now Pat. No. 6,617,311.

(30) Foreign Application Priority Data

Jun. 15, 1998 (NZ) ............................................. 330684

(51) Int. Cl.[7] .............................................. A61K 38/06
(52) U.S. Cl. ....................................................... 514/19
(58) Field of Search ................................... 514/18, 19

(56) References Cited

U.S. PATENT DOCUMENTS

| | | | |
|---|---|---|---|
| 5,714,460 A | 2/1998 | Gluckman et al. | 514/3 |
| 6,187,906 B1 | 2/2001 | Gluckman et al. | 530/331 |
| 6,294,585 B1 | 9/2001 | Brown | 514/279 |
| 6,617,311 B1 * | 9/2003 | Gluckman et al. | 514/19 |
| 6,682,753 B2 * | 1/2004 | Alexi | 424/422 |
| 6,780,848 B2 * | 8/2004 | Gluckman et al. | 514/18 |

FOREIGN PATENT DOCUMENTS

| | | |
|---|---|---|
| EP | 0 366 638 A2 | 5/1990 |
| WO | WO 95/17204 | 6/1995 |
| WO | WO 98/14202 | 4/1998 |

OTHER PUBLICATIONS

Sara, Vicki R., et. al., "The Biological Role of Truncated Insulin–like Growth Factor–1 and the Tripeptide GPE in the Central Nervous System", Annals of the New York Academy of Sciences, 692, 1993, 183–191.

Sara, Vicki R., et. al., "Identification of Gly–Pro–Glu (GPE), the Aminoterminal tripeptide of insulin–like growth factor 1 which is truncated in brain, as a novel neuroactive peptide", Biochemical and Biophysical Research Communications, vol. 165, No. 2, Dec. 15, 1989, 766–771.

Saura, J., et. al., "Neuroprotective effects of Gly–Pro–Glu, the N–terminal tripeptide of IGF–1, in the hippocampus in vitro", NeuroReport, vol. 10, No. 1, Jan. 1999, 161–164.

(Continued)

Primary Examiner—Jeffrey Edwin Russel
(74) Attorney, Agent, or Firm—Fliesler Meyer LLP (57) ABSTRACT

Embodiments of this invention include methods for increasing the amount of the enzyme tyrosine hydroxylase (TH) in the central nervous system (CNS) of mammals in need of an increase in TH. Methods include the use of the tripeptide, gly-pro-glu (GPE) to increase TH in the CNS. GPE can increase the amount of TH and/or decrease the loss of TH in conditions characterized by a loss of dopamine, such as Parkinson's disease and CNS injury. GPE may act to increase the expression of TH or by inhibiting a decrease in TH expression within the CNS or by inhibiting the loss of TH-containing neurons within the CNS. By increasing the amounts of TH in the CNS, GPE can increase the amount of the neurotransmitter, dopamine, in areas of the CNS responsible for adverse symptoms of neural injury or disease.

15 Claims, 5 Drawing Sheets

OTHER PUBLICATIONS

Nilsson–Hakansson, Lena et. al., "Effects of IGF–1, truncated IGF–1 and the tripeptide Gly–Pro–Glu on acetylcholine release from parietal cortex of rat brain", NeuroReport, vol. 4, No. 9, Aug. 1993, (Sep. Issue), 1111–1114.

Ludecke et al., "Recessively inherited L–DOPA–responsive parkinsonism in infancy caused by point mutation (L205P) in the tyrosine hydrolyse gene", Hum. Gen. 102:644–646 (1998).

Danks et al., "Tetrahydrobiopterin treatment of variant form of phenylketonuria", Lancet 2:1043, 1975.

Ludecke et al., A point mutation in the tyrosine hydroxylase gene associated with Segawa's syndrome, Hum. Gen. 93:123 (1995).

Mallet, "Tyrosine hydroxylase from cloning to neuropsychiatric disorders", Brain Research Bulletin 50(5,6): 381–382 (1992).

Guan et al., "N–terminal tripeptide of IGF–1 (GPE) prevents the loss of TH positive neurons after 6–OHDA induced nigral lesion in rats", Brain research Mar. 24, 2000 859(2), 286–92.

* cited by examiner

REGULATION OF TYROSINE HYDROXYLASE BY GPE

RELATED APPLICATIONS

This application is a continuation of U.S. application Ser. No. 09/719,459 filed Feb. 12, 2001, now U.S. Pat. Ser. No. 6,617,311, which claimed priority to PCT International Application Serial No. PCT/NZ99/00085, filed Jun. 15, 1999, which claimed priority to New Zealand Patent Application Serial No. 330,684, filed Jun. 15, 1998. Each of the above applications is incorporated herein fully by reference.

This invention relates to methods of regulating the effect of tyrosine hydroxylase (TH). In particular it relates to increasing the effective amount of TH in the central nervous systems (CNS) for the purpose of increasing TH-mediated dopamine production in the treatment of conditions such as Parkinson's disease.

BACKGROUND

Parkinson's disease is the second most prevalent neurodegenerative disorder after Alzheimer's. It is a chronic and progressive motor system disorder and is distinguished by a tremor at rest, muscular rigidity, a slowness of movement initiation and movement execution and a mask-like appearance to the face.

The cause of this disease is unknown but the symptoms are a consequence of an 80% or greater loss of the dopaminergic neurons (which produce dopamine) in the pars compacta region of the substantia nigra (SNc).

Treatments available at present only target symptoms of the disease. No drugs are currently available to intervene in the disease process. L-dopa is the most commonly employed current treatment (in order to supplement dopamine levels within the CNS), but this has limited and transient efficacy.

TH is a rate limiting enzyme for dopamine production. Upregulation of TH expression will therefore increase dopamine production in the CNS.

GPE is a tripeptide consisting of amino acids Gly-Pro-Glu. It and its dipeptide analogs Gly-Pro and Pro-Glu were first disclosed by Sara et al in EP 0366638. The suggestion made by Sara et al is that GPE has neuromodulatory properties. GPE has also been established as having neuroprotective properties and therefore having utility in the prevention or inhibition of neural cell death (WO 95/17204).

To date however, there has been no teaching or suggestion of GPE or its analogs having any direct effect on the effective amount of TH present in the CNS or being able to intervene in the Parkinson's disease process.

OBJECT OF THE INVENTION

It is an object of this invention to provide new approaches to therapy or prophylaxis which involve directly upregulating the expression of TH and TH-mediated dopamine production in CNS, or at least to provide the public with a useful choice.

SUMMARY OF THE INVENTION

In a first aspect, the invention provides a method of treatment of a patient suffering from or susceptible to a condition in which an increase in the amount of TH present within the CNS is desirable, which method comprises the step of increasing the effective amount of GPE or an analog thereof within the CNS of said patient.

In a further aspect, the invention provides a method of effecting an increase in the amount of TH within the CNS of a patient for therapy or prophylaxis of a neurological disorder or condition involving dopaminergic neurons, said method comprising the step of increasing the effective amount of GPE or an analog thereof within the CNS of said patient.

An "increase in the amount of TH" can be effected through upregulation of expression of TH or a reduction in the loss or degradation of TH.

By "analog" it is meant the dipeptides Gly-Pro and Pro-Glu as well as any other small peptide which is capable of effectively binding to the receptors in the CNS GPE binds to and of inducing an equivalent upregulatory effect upon the expression of TH.

In still a further aspect, the invention provides a method of increasing TH-mediated dopamine production within the CNS of a patient, said method comprising the step of increasing the effective amount of GPE or an analog thereof within the CNS of said patient.

Most preferably, it is the effective amount of GPE itself which is increased within the CNS of the patient. This can be effected by direct administration of GPE and indeed this is preferred. However, the administration of compounds which indirectly increase the effective amount of GPE (for example a pro-drug which, within the patient is cleaved to release GPE) is in no way excluded.

The active compound (GPE or its analog) can be administered alone, or as is preferred, as part of a pharmaceutical composition.

The composition can be administered to the patient peripherally (for example by a parenteral route such as injection into the peripheral circulation) or can be administered directly to the CNS. This latter route of administration can involve, for example, lateral cerebro-ventricular injection, focal injection or a surgically inserted shunt into the lateral cerebro-ventricle of the brain of the patient.

Conveniently, the amount of TH is increased through the administration of GPE or its analogs in the prophylaxis or therapy of Parkinson's disease.

It is also preferred that the increase of TH-mediated dopamine production is effected as part of therapy or prophylaxis of Parkinson's disease.

In a further aspect, the invention also consists in the use of GPE or an analog thereof in the manufacture of a medicament for use in increasing the amount of TH present in the CNS of a patient.

In still a further aspect, the invention consists in the use of GPE or an analog thereof in the manufacture of a medicament for use in increasing TH-mediated dopamine production for treating Parkinson's disease.

BRIEF DESCRIPTION OF THE DRAWINGS

The present invention is broadly as defined above. However, those persons skilled in the art will appreciate that it is not limited only to the above but that it also includes embodiments of which the following description provides examples. A better understanding of the present invention will also be gained through reference to the accompanying drawings in which.

DESCRIPTION OF THE INVENTION

As indicated above, the present invention is broadly based upon the applicants surprising finding that GPE and its analogs are capable of increasing the amount of TH within the CNS. This increase, which is through upregulating TH expression or through preventing the loss or degradation of TH, is achieved through increasing the effective concentration or amount of GPE or the analog in the CNS of a patient.

The effective increase in the amount of TH in turn effects an increase in the production of dopamine within the CNS.

It is presently preferred by the applicants that GPE itself be used to increase the amount of TH/dopamine. Most conveniently, this is effected through the direct administration of GPE to the patient.

However, while this is presently preferred, there is no intention on the part of the applicants to exclude administration of other forms of GPE. By way of example, the effective amount of GPE in the CNS can be increased by administration of a prodrug form of GPE which comprises GPE and a carrier, GPE and the carrier being joined by a linkage which is susceptible to cleavage or digestion within the patient. Any suitable linkage can be employed which will be cleaved or digested to release GPE following administration.

Another option is for GPE levels to be increased through an implant which is or includes a cell line which is capable of expressing GPE in an active form within the CNS of the patient.

GPE can be directly administered as part of a medicament or pharmaceutical preparation. This can involve combination of GPE with any pharmaceutically appropriate carrier, adjuvant or excipient. The selection of the carrier, adjuvant or excipient will of course usually be dependent upon the route of administration to be employed.

The administration route can vary widely. An advantage of GPE is that it can be administered peripherally. This means that it need not be administered directly to the CNS of the patient in order to have effect in the CNS.

Any peripheral route of administration known in the art can be employed. These can include parenteral routes with injection into the peripheral circulation being a suitable example. However, alternative administration routes selected from oral, rectal, nasal, subcutaneous, inhalation, intraperitonial or intramuscular can be employed.

Two of the most convenient administration routes will be by subcutaneous injection (eg. dissolved in 0.9% sodium chloride) or orally (in a capsule).

It will also be appreciated that it may on occasion be desirable to directly administer GPE to the CNS of the patient. Again, this can be achieved by any appropriate direct administration route. Examples include administration by lateral cerebro-ventricular injection or through a surgically inserted shunt into the lateral cerebro-ventricle of the brain of the patient.

The calculation of the effective amount of GPE or its analogs to be administered will be routine to those persons skilled in this art. Needless to say, the final amount to be administered will be dependent upon the route of administration and upon the nature of the neurological disorder or condition which is to be treated. A suitable dose range may for example be between about 0.04 mg to 1000 mg of GPE and/or analog per 100 g of body weight where the dose is administered centrally.

For inclusion in a medicament, GPE and its analogs can be obtained from a suitable commercial source. Alternatively, GPE and its analogs can be directly synthesised by conventional methods such as the stepwise solid phase synthesis method of Merryfield et al. (*J. Amer. Chem. Soc.* 85 2149–2156 (1963)) Alternatively, synthesis can involve the use of commercially available peptide synthesisers such as the Applied Biosystems model 430A.

The present invention will now be illustrated with reference to the following nonlimiting examples.

EXAMPLE 1

This experiment was blind with respect to the treatment (with GPE or the vehicle) and with respect to the counting of neurons expressing TH (between sections from animals treated with GPE or vehicle).

The objective of this experiment was to determine the effects of administering GPE on the expression of tyrosine hydroxylase (TH) in the presence or absence of CNS injury. The experiment involved treating the rats with a control vehicle or GPE 2 hours after a chemically induced lesion in the substantia nigra region of the brain. Specifically, 9 pairs of adult male Wistar rats (280–320 g) were prepared under 3% halothane/$O_2$ anaesthesia. The oxygen free radical producing neurotoxin 6-hydroxydopamine (6-OHDA) which produces degeneration of dopamine neurones (8 µg/2 µl) was injected into the median forebrain bundle using a 30 gauge needle (coordinates: anterior-posterior +4.7 mm, right +1.6 mm, vertical –8.5 mm). A guide cannula was placed on the dura 7.5 mm anterior from stereotaxic zero and 1.5 mm from the midline on the right. The rats were left to recover at room temperature. 2 hours after the administration of 6-OHDA the rats were treated, via the guide cannula, with 3µg GPE or vehicle alone (15µl injected with a pump rate of 2 µl/minute, 0.1M acetate buffer [pH6], diluted 10 times in 0.1 bovine serum albumin in 0.1M phosphate buffered saline [PBS][pH7.31]).

The rats were sacrificed using pentobarbital 14 days after 6-OHDA induced injury. Brains were perfused with normal saline and 4% paraformaldehyde and fixed in perfusion fixative overnight. The brains were paraffin embedded using a standard processing schedule. Sections (8 µm) were cut through the substantia nigra using a microtome. Immunoreactivity for TH was established with sections mounted on chrome alum coated slides. Briefly, the sections were dewaxed, rehydrated and washed in 0.1M PBS. The sections were pre-treated with 1% $H_2O_2$ in 50% methanol for 20 minutes and then washed in 0.1M PBS (5 minutes×3). The antibodies were diluted in 1% goat serum. The sections were then incubated with rabbit (Rb) anti-TH (1:500) antibodies (the primary antibodies) for 2 days. The sections were washed using 0.1M PBS (5 minutes×3) and then incubated with goat anti-rabbit biotinylated secondary antibodies (1:200) at room temperature overnight. The sections were washed in 0.1M PBS (5 minutes×3) and then incubated in (ExtrAvidin TM Sigma 1:200) for 3 hours and followed by $H_2O_2$ (0.01%) in 3,3-diaminobenzidine tetrahydrochloride (DAB, 0.05%) reaction. The sections were then dehydrated and coverslipped.

The neurons in the pars compacta region of the SNc at 3 levels in both hemispheres which showed specific immunoreactivities corresponding to TH were counted using a light microscope. The total counts of neurons were compared between the GPE and the vehicle treated group. Data were analysed with paired t-test and presented as mean±sem. The results are presented in FIG. 1.

Figure 1:
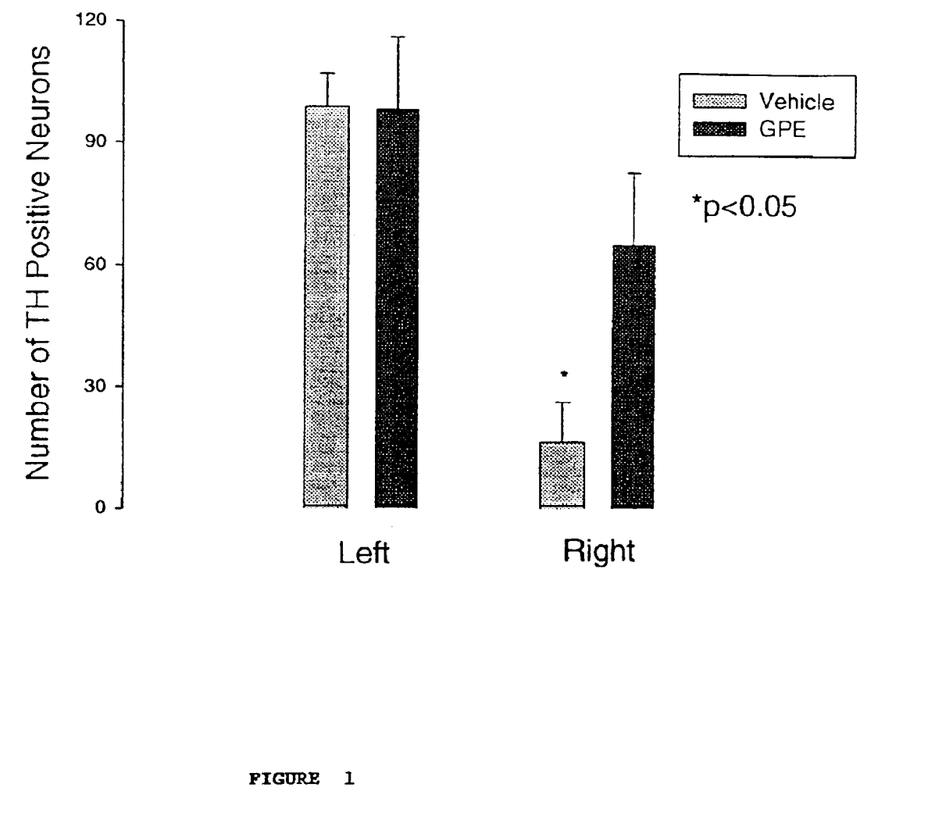
FIG. 1 shows the number of TH immunopositive neurons following treatment with a control vehicle or with GPE two hours after administration of a neuro-toxin.

FIG. 1 shows that the number of TH immunopositive dopaminergic neurons increased with GPE on the lesioned (right) side of the brain. This indicates that the administration of GPE is effective in upregulating TH expression.

EXAMPLE 2

Example 2 was performed using a second set of rats (9 pairs), using the same experimental parameters except that only the immunopositive neurons at 2 levels of the SNc were counted.

Figure 2:
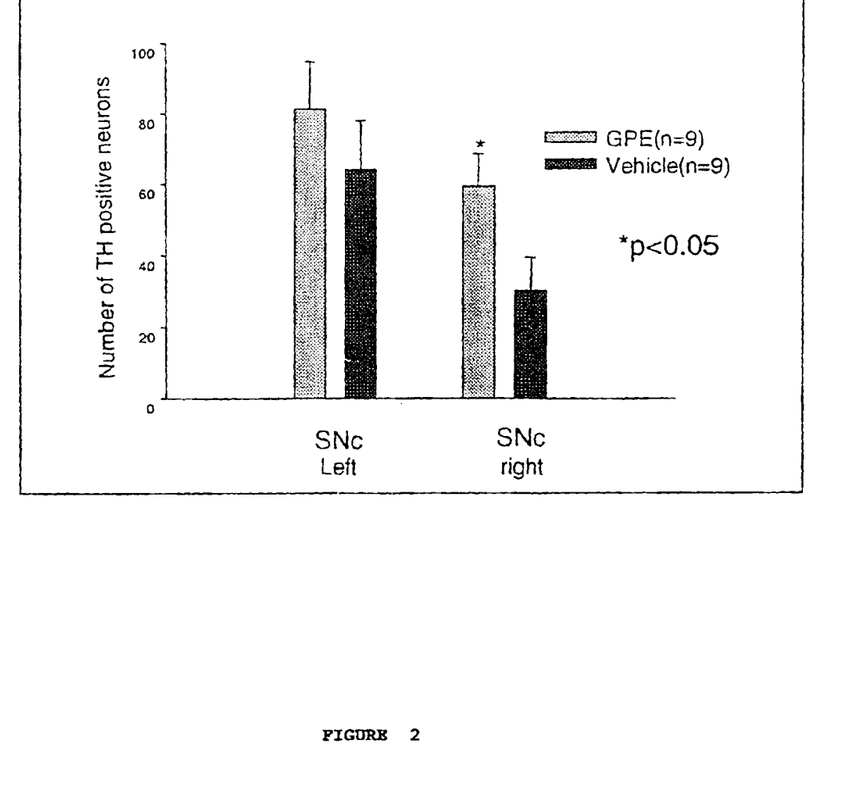
FIG. 2 shows the number of TH immunopositive neurons following treatment with a control vehicle or with GPE two hours after administration of a neuro-toxin.

The results are shown in FIG. 2, and again demonstrated upregulation of TH expression.

EXAMPLE 3

Ethics Approval

These experiments were approved by the University of Auckland Animal Ethics Committee and all efforts were made to minimise the suffering incurred and the numbers of animals used.

Experimental Design and Animal Preparation

A paired experimental design was used and the experimenter was blinded to the treatment groups. Eighteen male Wistar rats (50–60 days old, 280–310 g) were used for this study. 6-hydroxy dopamine (6-OHDA) was prepared as 8 μg in a base of 2 μl 0.9% saline containing 1% ascorbic acid. It was administered into the right medial forebrain bundle (MFB) using coordinates of AP+4.7 mm, R 1.6 mm, V–8 mm under anaesthesia of 3% halothane. 6-OHDA was injected into the right MFB using a Hamilton syringe (100 μl with a 30G needle) controlled by a microdialysis infusion pump at an infusion rate of 0.2 μl/minute. The infusion needle was then slowly withdrawn 5 minutes after the infusion. The surgery and procedures for the intracerebroventricular administration have been described by Guan et al (1993), *Journal of Cerebral Blood Flow and Metab*, 13, 609–616. Briefly, a guide cannula (21G, 6 mm) was fixed on the top of the dura with coordinates of AP+7.5 mm, R 1.5 mm immediately after the injection of 6-OHDA. Either GPE (3 μg/15 μl) or its vehicle were infused into the right lateral ventricle 2 hours later at an infusion rate of 2 μl/minute. Rats were then housed in a holding room with food and water ad libitum for the next 2 weeks.

The rats were then deeply anaesthetized with an overdose of pentobarbital and transcardially perfused with normal saline followed by 10% buffered formalin. The brains were removed from the skull and kept in the same fixative for the next 48 hours. A standard paraffin tissue preparation was used to process the tissue so that it could be used for immunohistochemistry. Coronal sections (8 μm) were cut using a microtome, and the sections were mounted on chrome alum coated microscopy slides and air-dried. SNc sections used for immunohistochemical staining were deparaffinized, rehydrated and washed in PBS (0.1M). The sections were then pretreated with 1% $H_2O_2$ for 20 minutes, washed with 0.1M PBS (3×5 minutes) and incubated with rabbit polyclonal antisera raised against tyrosine hydroxylase (Protos Biotech, USA) diluted 1:500 with 1% goat serum for 48 hours at 4° C. The sections were washed in PBS (3×5 minutes) and incubated with donkey anti-rabbit biotinylated secondary antibody (1:200, Amersham, Life Science) overnight at room temperature. The sections were washed, incubated in streptavidin-biotinylated horseradish peroxidase (1:200, Amersham, Life Science) for 3 hours, washed again in PBS and then reacted in 0.05% 3,3-diaminobenzidine tetrahydrochloride (DAB) and 0.01% $H_2O_2$ to produce a brown reaction product. The sections were dehydrated in a graded alcohol series, cleared in xylene and coverslipped with mounting medium.

Tissue Evaluation and Statistics

The number of TH positive neurons on both sides of the SNc were counted using light microscopic examination (20× magnification) at three representative levels (AP+4.2, +3.8 mm and 3.4 mm) (Paxinos, et al (1982), New York: Academic Press). The average density from the background was also measured. The analyst was blinded to the treatment and control groups. The difference in average density between the background and TH immunostaining was calculated and used for data analysis. Right/left (R/L) ratios of both the number of TH immunopositive neurons and the average density of TH immunostaining from each level was compared between the two treatment groups using one way ANOVA. Data are presented as mean±SEM.

Results

Figure 3:
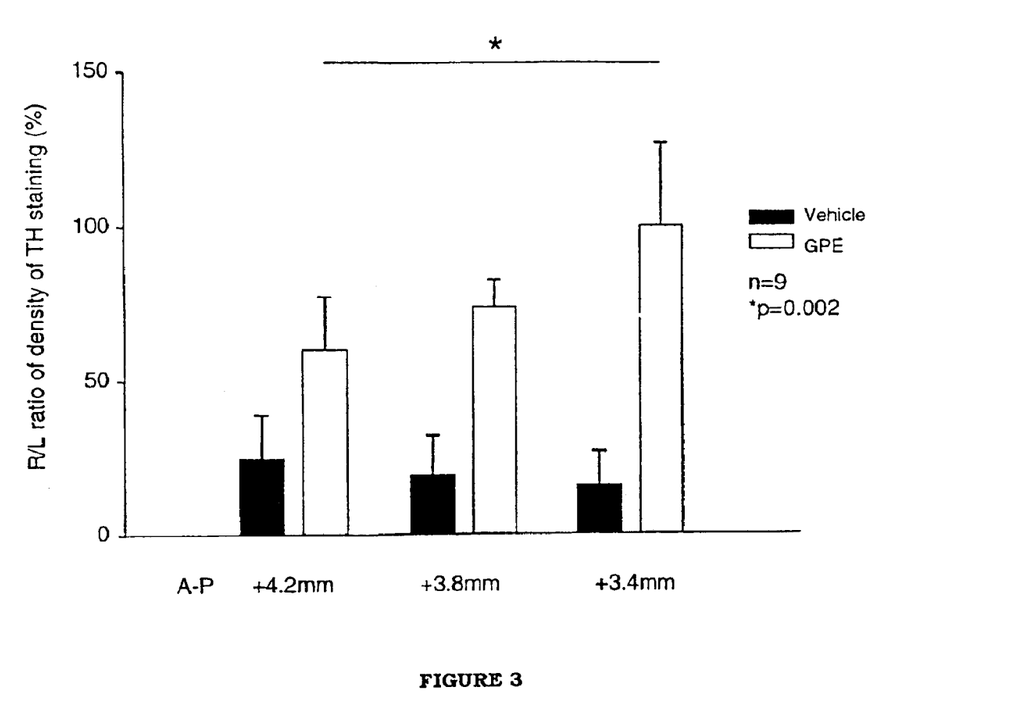
FIG. 3 shows the density of TH immunopositive staining following treatment with a control vehicle or with GPE two hours after administration of a neuro-toxin.

FIG. 3 shows that TH immunoreactivity was restored with GPE on the lesioned (right) side of the brain. This effect was more pronounced in caudal levels (16±11.2 to 99.6±27%) compared with the rostral level (FIG. 3). This indicates that the administration of GPE is effective and selective in upregulating TH expression.

Figure 4:
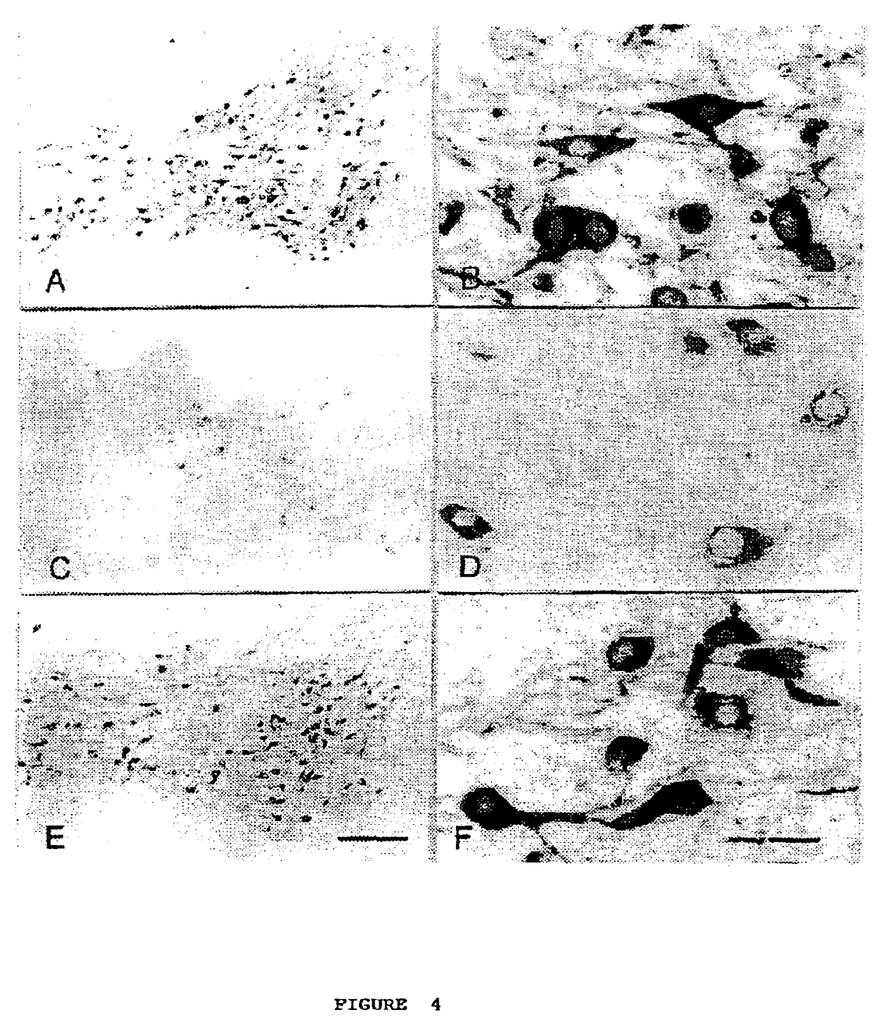
FIG. 4 shows photomicrographs of immunohistochemical labeling of the SNc with an antibody against TH. A, C and E are at 10× magnification and B, D and F are at 40× magnification. A and B are photomicrographs of control sections of the right side of the SNc. C and D are photomicrographs from ipsilateral SNc where the vehicle was administered intraventricularly 2 hours after lesioning with 6-OHDA. Note the major decrease in TH immunoreactivity in C and the decreased immunoreactivity in the cell body and processes in D. E and F are photomicrographs of the ipsilateral SNc where GPE was administered intraventricularly 2 hours after lesioning with 6-OHDA. Scale bars A, C, E=0.5 µm, B, D, F=20 µm.

GPE treatment restored the density of TH immunostaining in both the cytoplasm and processes of neurons (FIG. 4).

GPE also showed 99.6±27.0% restoration in TH immunoreactivity with only 60±13.0% neuronal survival in the most caudal level analysed of the SNc.

DISCUSSION/CONCLUSIONS

The above example shows the effect of GPE administration on TH expression in the SNc. GPE was particularly effective in upregulating TH expression in the most caudal region of SNc analysed. GPE upregulated TH expression in the cytoplasm of both the neuronal cell body and neuronal processes. GPE prevented the loss of TH immunopositive neurons in the SNc compared to the control group. GPE provided protection for the dopaminergic neurons against the neurotoxin 6-OHDA.

EXAMPLE 4

Ethics Approval

These experiments were approved by the University of Auckland Animal Ethics Committee and all efforts were made to minimise the suffering incurred and the numbers of animals used.

Medial Forebrain Bundle Transection and Cannulation

Adult male Wistar rats (200–220 g) were anaesthetized with 75 mg/kg Nembutal and positioned in a stereotaxic apparatus. Unilateral transection of the medial forebrain bundle which contains the ascending nigral dopaminergic projection fibers was made 1.3 mm rostral to the rostral tip of the SNc using a retractable wire knife (David Kopf Instruments, Tujunga, Calif.). The knife was lowered into the brain using the following coordinates from the atlas of Paxinos and Watson (1986), Sydney: Academic Press: 3.3 mm posterior to Bregma, 2.4 mm lateral from midline, and 8.5 mm ventral from skull, the blade was extended 2.0 mm toward midline, raised 2.5 mm dorsally, retracted and extended again, and then returned 2.5 mm ventrally. The wire blade was retracted and the knife withdrawn. Next, a 22-gauge metal guide cannula was permanently fixed into place supranigrally at 5.0 mm posterior to Bregma, 2.0 mm lateral to midline, and 6.8 mm ventral to skull. A second set of intact unlesioned rats were cannulated supranigrally at the same coordinates.

Neurotrophic Factor Infusion

Animals received daily supranigral injections of trophic factors via a Hamilton syringe attached to a 28-gauge cannula 1 µl of either GPE (0.3 µg/µl), or 1 µg of the control vehicle PBS with 0.1% bovine serum albumin (BSA) beginning immediately after lesioning and extending for two weeks post-lesioning. GPE was diluted in phosphate buffered saline (PBS) containing 0.1% BSA (pH 7.4).

Immunocytochemistry

After two weeks of treatment, animals were perfused under deep anaesthesia with PBS (pH 7.4) followed by 4% paraformaldehyde in phosphate buffer (pH 7.4). Brains were post-fixed for 24 hours at 4° C. in the same fixative then transferred sequentially to 10% and 30% sucrose in PB for 2–5 days until sunken. Floating 30 µm coronal nigral sections were stained by avidin-biotin-peroxidase immunocytochemistry. Rabbit anti-rat tyrosine hydroxylase (TH) polyclonal antibody (TE101, Eugene Tech International, New Jersey, USA) was diluted 1:100 in PBS containing 0.2% Triton X-100, 3% goat serum, and 0.02% sodium azide. Sections were first incubated for 1 hour at room temperature in primary antibody vehicle. Incubation with the primary antibody was for 3–4 days at 40° C. Biotinylated anti-rabbit IgG (Vector Laboratories) secondary antibody was diluted at 4 µl/ml in PBS containing 0.1% Triton X-100 and normal rabbit serum. Sections were incubated for 2 hours at room temperature, followed by an avidin-biotin-peroxidase cocktail (Vector Laboratories) incubation for 1 hour at room temperature. Peroxidase was visualized with 1 mg/ml 3,3'-diaminobenzidine in 0.03% $H_2O_2$ for 5 minutes. Controls were conducted by replacing the primary antibody with pre-immune IgG or by omitting the primary and/or secondary antibody from the procedure. Sections were mounted on gelatin-coated slides, dehydrated in serial ethanol, cleared in xylene and coverslipped with mounting media.

Quantificaton of Cell Number

Immunopositive cells were counted in the central SNc Counts were made ventral and lateral to the lemniscus medialis, including both the pars compacta and pars reticulata, but excluding the ventral tegmental area in the ventromedial midbrain and the retrorubral field in the caudolateral midbrain. A cell was counted if it had an intact cell body and soma membrane. Counts were taken on both the contralateral and ipsilateral sides from 2–3 animals per treatment. The number of cells was represented by the mean number of immunopositive cells within the described field on each side of the brain. To reveal percent survival, percent changes were calculated by dividing the ipsilateral value by contralateral value.

Results

Figure 5:
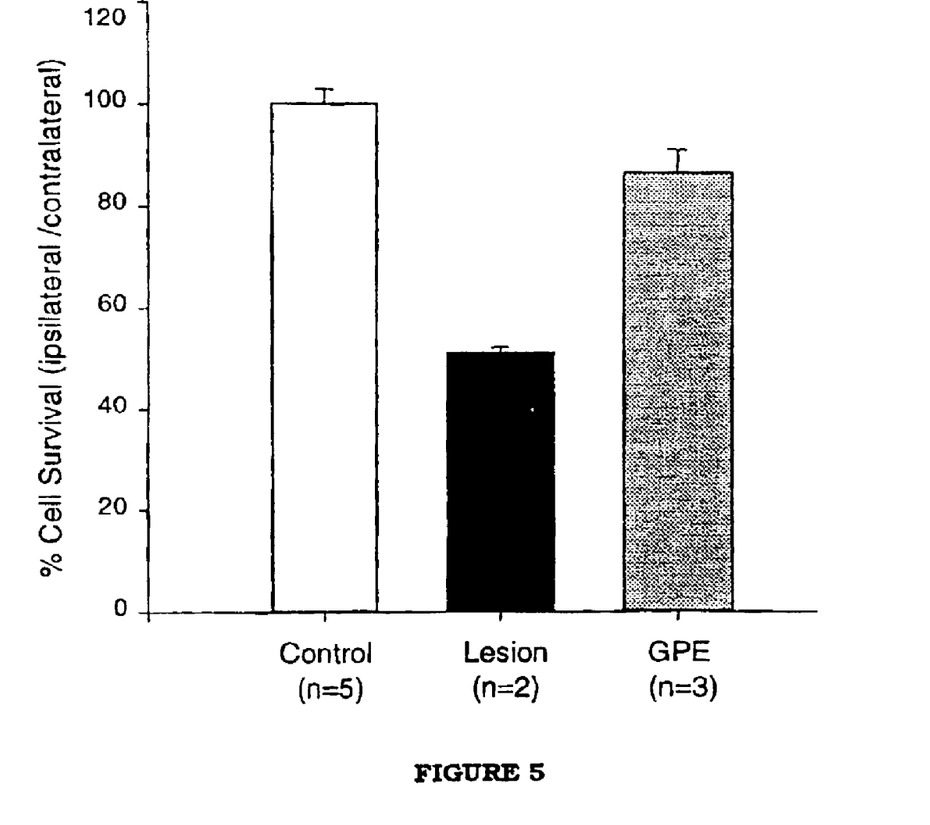
FIG. 5 shows cell counts expressed as percent cell survival of substantia nigra neurons after mechanical lesioning and treatment with GPE.

The percent cell survival of TH immunopositive neurons increased with GPE treatment on the lesioned side of the brain (FIG. 5). This indicates GPE is effective in upregulating TH expression.

Discussion

The above examples show the effect of GPE administration on TH expression in the pars compacta region of the SNc.

INDUSTRIAL APPLICATION

The experimental results demonstrate the ability of GPE to increase the amount of TH in the CNS through a direct increase in enzyme expression. In turn, the increased expression of TH leads to an increase in TH-mediated dopamine production.

These findings make GPE and its analogs applicable in treating a number of neurological disorders or conditions, either therapeutically or prophylactically. Indeed, it will be apparent to those persons skilled in the art that GPE and its analogs can be employed at any time where a patient would benefit from an increase in the expression of TH/dopamine within the CNS. Neurological disorders or conditions which would benefit from this include, but are not limited to Parkinson's disease.

It will be appreciated that although the present invention is described above with reference to certain specific embodiments, the description provided is exemplary only and that the invention is not limited thereto.

What is claimed is:

1. A method of treatment of a patient suffering from or susceptible to a condition in which an increase in the amount of tyrosine hydroxylase (TH) with the central nervous system (CNS) of said patient is desirable, which method comprises the step of effecting an increase in the amount of TH within the CNS through increasing the effective amount of GPE within the CNS of said patient.

2. A method of effecting an increase in the amount of tyrosine hydroxylase (TH) within the CNS of a patient for therapy or prophylaxis of a neurological disorder or condition involving dopaminergic neurons, said method comprising the step of increasing the effective amount of GPE within the CNS of the patient.

3. A method of treatment of a patient suffering from or susceptible to a condition in which an increase of tyrosine hydroxylase (TH)-mediated dopamine production is desirable, which method comprises the step of effecting an increase in the amount of TH produced through increasing the effective amount of GPE within the CNS of said patient.

4. The method of treatment as claimed in claim 1 wherein the concentration of GPE is increased by administering to said patient an effective amount of GPE.

5. The method of treatment as claimed in claim 1 wherein the concentration of GPE is increased in the CNS by direct administration of GPE.

6. The method as claimed in claim 1 which is prophylactic.

7. The method as claimed in claim 1 which is therapeutic.

8. A method of treatment or prophylaxis of Parkinson's disease in a patient, which method comprises increasing tyrosine hydroxylase (TH)-mediated dopamine production by dopaminergic neurons within the substantia nigra of the CNS by the step of increasing the effective amount of GPE within the CNS of said patent.

9. The method of claim 1, wherein said condition is Parkinson's disease.

10. The method of claim 2, wherein said condition is Parkinson's disease.

11. The method of claim 3, wherein said condition is Parkinson's disease.

12. The method of claim 1, wherein said GPE is administratered via one or more routes selected from the group consisting of lateral cerebro-ventricular injection, focal injection, subcutaneous injection, intraperitoneal injection, intramuscular injection, oral administration, rectal administration, nasal administration and inhalation.

13. The method of claim 1, wherein said GPE is administered parenterally.

14. The method of claim 8, wherein said GPE is administered via one or more routes selected from the group consisting of lateral cerebro-ventricular injection, focal injection, subcutaneous injection, intraperitoneal injection, intramuscular injection, oral administration, rectal administration, nasal administration and inhalation.

15. The method of claim 8, wherein said GPE is administered. parenterally.

* * * * *